United States Patent
Malavalli et al.

(10) Patent No.: US 9,493,616 B2
(45) Date of Patent: Nov. 15, 2016

(54) METHODS FOR PREPARING PEG-HEMOGLOBIN CONJUGATES USING REDUCED REACTANT RATIOS

(75) Inventors: Ashok Malavalli, San Diego, CA (US); Kim D. Vandegriff, San Diego, CA (US)

(73) Assignee: Sangart, Inc., San Diego, CA (US)

( * ) Notice: Subject to any disclaimer, the term of this patent is extended or adjusted under 35 U.S.C. 154(b) by 0 days.

(21) Appl. No.: 13/579,656

(22) PCT Filed: Feb. 23, 2011

(86) PCT No.: PCT/US2011/025888
§ 371 (c)(1),
(2), (4) Date: Dec. 5, 2012

(87) PCT Pub. No.: WO2011/106396
PCT Pub. Date: Sep. 1, 2011

(65) Prior Publication Data
US 2013/0217860 A1    Aug. 22, 2013

Related U.S. Application Data

(60) Provisional application No. 61/308,238, filed on Feb. 25, 2010.

(51) Int. Cl.
| | | |
|---|---|---|
| *C08H 1/00* | (2006.01) | |
| *A61K 47/48* | (2006.01) | |
| *C07K 14/80* | (2006.01) | |
| *C07K 14/805* | (2006.01) | |
| *A61K 38/00* | (2006.01) | |

(52) U.S. Cl.
CPC ........... *C08H 1/00* (2013.01); *A61K 47/48215* (2013.01); *C07K 14/805* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,001,200 A | 1/1977 | Bonsen et al. | |
| 4,001,401 A | 1/1977 | Bonsen et al. | |
| 4,301,144 A | 11/1981 | Iwashita et al. | |
| 4,412,989 A | 11/1983 | Iwashita et al. | |
| 4,529,719 A | 7/1985 | Tye | |
| 4,670,417 A | 6/1987 | Iwasaki et al. | |
| 5,234,903 A | 8/1993 | Nho et al. | |
| 5,296,465 A | 3/1994 | Rausch et al. | |
| 5,585,484 A | 12/1996 | Acharya et al. | |
| 5,650,388 A | 7/1997 | Shorr et al. | |
| 5,661,124 A | 8/1997 | Hoffman et al. | |
| 6,054,427 A | 4/2000 | Winslow | |
| 6,844,317 B2 | 1/2005 | Winslow et al. | |
| 7,501,499 B2 | 3/2009 | Acharya et al. | |
| 2003/0153491 A1 | 8/2003 | Winslow et al. | |
| 2006/0135753 A1* | 6/2006 | Acharya et al. | 530/385 |
| 2006/0172924 A1 | 8/2006 | Winslow et al. | |
| 2006/0234915 A1 | 10/2006 | Winslow | |
| 2010/0075379 A1 | 3/2010 | Vandegriff et al. | |
| 2013/0041134 A1 | 2/2013 | Handley et al. | |

FOREIGN PATENT DOCUMENTS

| | | |
|---|---|---|
| DE | 2 161 086 | 12/1971 |
| DE | 2 449 885 | 10/1974 |
| DE | 3 026 398 | 7/1980 |
| WO | 2008/136888 A2 | 11/2008 |

OTHER PUBLICATIONS

Vandegriff et al., "MP4, a new nonvasoactive PEG-Hb conjugate", Transfusion 2003;43:509-516.*
Acharya, S. A., et al., "Enhanced Molecular Volume of Conservatively Pegylated Hb: (SP-PEG5K)6-HbA is Non-Hypertensive," Artificial Cells, Blood Substitutes, and Immobilization Biotechnology, 2005, p. 239-255, vol. 33, No. 3.
Amberson, W. R., "Clinical Experience with Hemoglobin-Saline Solutions," Science, Aug. 8, 1947, p. 117, vol. 106, No. 2745.
Benesch, R., et al., "Hemoglobin Covalently Bridged Across the Polyphosphate Binding Site," Biochemical and Biophysical Research Communications, 1975, pp. 1123-1129, vol. 63, No. 4.
Blumenstein, J., et al., "Experimental Transfusion of Dextran-Hemoglobin," Blood Substitutes and Plasma Expanders, 1978, pp. 205-212, vol. 19.
Bunn, H. F., et al., "The Renal Handling of Hemoglobin. I. Glomerular Fitration," The Journal of Experimental Medicine, May 1969, pp. 909-924, vol. 129, No. 5.
Chang, J. E., et al., "Synthesis of Soluble Dextran-Hemoglobin Complexes of Different Molecular Sizes," Canadian Journal of Biochemistry, 1977, pp. 398-403, vol. 55, No. 4.
Doherty, D. H., et al., "Rate of Reaction with Nitric Oxide Determines the Hypertensive Effect of Cell-Free Hemoglobin," Nature Biotechnology, Jul. 1998, pp. 672-676, vol. 16, No. 7.
Dust, J. M., et al., "Proton NMR Characterization of Poly(ethylene glycols) and Derivatives," Macromolecules, 1990, pp. 3742-3746, vol. 23, No. 16.
Eich, R. F., et al., "Mechanism of NO-Induced Oxidation of Myoglobin and Hemoglobin," Biochemistry, 1996, pp. 6976-6983, vol. 35, No. 22.
Furchgott, R. F., "The Role of Endothelium in the Responses of Vascular Smooth Muscle to Drugs," Annual Review of Pharmacology and Toxicology, 1984, pp. 175-197, vol. 24.
Hess, J. R., et al., "Pulmonary and Systemic Hypertension After Hemoglobin Administration," Poster Session IV: Transfusion, Meeting Abstract 1414, Blood, 1991, p. 356A, vol. 78.
Hess, J. R., et al., "Systemic and Pulmonary Hypertension After Resuscitation with Cell-Free Hemoglobin," Journal of Applied Physiology, Apr. 1993, pp. 1769-1778, vol. 74, No. 4.

(Continued)

Primary Examiner — Suzanne M Noakes
(74) Attorney, Agent, or Firm — Senniger Powers LLP

(57) ABSTRACT

The present invention relates generally to methods for preparing polyethylene glycol ("PEG") conjugated hemoglobin ("Hb") using reduced reactant ratios. More specifically, the present invention relates to methods for preparing PEG conjugated Hb ("PEG-Hb") with enhanced yield and purity.

18 Claims, 1 Drawing Sheet

(56) References Cited

OTHER PUBLICATIONS

Imai, K., "Analyses of Oxygen Equilibria of Native and Chemically Modified Human Adult Hemoglobins on the Basis of Adair's Stepwise Oxygenation Theory and the Allosteric Model of Monod, Wyman, and Changeux," Biochemistry, 1973, pp. 798-808, vol. 12, No. 5.

Iwashita, Y., et al., "Renal Toxicity of Hemoglobin Derivatives as Blood Substitute," Organ-Directed Toxicity Chemical Indices and Mechanisms, Proceedings of the Symposium on Chemical Indices and Mechanisms of Organ-Directed Toxicity, Presented in Barcelona, Spain, Mar. 4-7, 1981, pp. 97-101.

Juszczak, L. J., et al., "UV Resonance Raman Study of beta93-Modified Hemoglobin A: Chemical Modifier-Specific Effects and Added Influences of Attached Poly(ethylene glycol) Chains," Biochemistry, 2002, pp. 376-385, vol. 11, No. 1.

Keipert, P. E., et al., "Acute Changes in Systemic Blood Pressure and Urine Output of Conscious Rats Following Exchange Transfusion With Diaspirin-Crosslinked Hemoglobin Solution," Transfusion, 1993, pp. 701-708, vol. 33, No. 9.

Kilbourn, R. G., et al., "Cell-Free Hemoglobin Reverses the Endotoxin-Mediated Hyporesponsivity of Rat Aortic Rings to alpha-adrenergic Agents," Biochemical and Biophysical Research Communications, Feb. 1994, pp. 155-162, vol. 199, No. 1.

Lemon, D. D., et al., "Control of the Nitric Oxide-Scavenging Activity of Hemoglobin," Biotechnology, 1996, p. 378, vol. 24.

Li, D., et al., "Extension Arm Facilitated PEGylation of Hemoglobin: Correlation of the Properties with the Extent of PEGylation," The Protein Journal, Jun. 2006, pp. 263-274, vol. 25, No. 4.

Liebhaber, S. A., et al., "Cloning and Complete Nucleotide Sequence of Human 5'-alpha-globin Gene," Proceedings of the National Academy of Sciences of the United States of America, Dec. 1980, pp. 7054-7058, vol. 77, No. 12.

Macdonald, V. W., et al., "Vasoconstrictor Effects in Isolated Rabbit Heart Perfused with bis(3,5-dibromosalicyl) Fumarate Cross-Linked Hemoglobin (alpha alpha Hb)," Artificial Cells, Blood Substitutes, and Immobilization Biotechnology, 1994, pp. 565-575, vol. 22, No. 3.

Manjula, B. N., et al., "Conjugation of Multiple Copies of Polyethylene Glycol to Hemoglobin Facilitated Through Thiolation: Influence on Hemoglobin Structure and Function," The Protein Journal, Apr. 2005, pp. 133-146, vol. 24, No. 3.

Marotta, C. A., et al., "Human Beta-Globin Messenger RNA," The Journal of Biological Chemistry, Jul. 25, 1977, pp. 5040-5053, vol. 252, No. 14.

Muldoon, S. M., et al., "Hemoglobin-Induced Contraction of Pig Pulmonary Veins," The Journal of Laboratory and Clinical Medicine, Dec. 1996, pp. 579-584, vol. 128, No. 6.

Perutz, M. F., et al., "Influence of Globin Structure on the State of the Heme. I. Human Deoxyhemoglobin," Biochemistry, 1974, pp. 2163-2173, vol. 13, No. 10.

Rabiner, S. F., et al., "Evaluation of a Stroma-Free Hemoglobin Solution for Use as a Plasma Expander," The Journal of Experimental Medicine, Dec. 1967, pp. 1127-1142, vol. 126, No. 6.

Rohlfs, R. J., et al. "Arterial Blood Pressure Responses to Cell-Free Hemoglobin Solutions and the Reaction with Nitric Oxide," The Journal of Biological Chemistry, May 1998, pp. 12128-12134, vol. 273, No. 20.

Simon, S. R., et al., "Chemical Modification of Hemoglobins: A Study of Conformation Restraint by Internal Bridging," Proceedings of the National Academy of Sciences of the United States of America, Aug. 1966, pp. 749-756, vol. 56, No. 2.

Supplementary European Search Report issued for EP 11747978.2 on Feb. 1, 2016, 7 pages.

Vandegriff, K D., et al., "Hemoglobin—Oxygen Equilibrium Binding: Rapid-Scanning Spectrophotometry and Singular Value Decomposition," Methods in Enzymology, 1994, pp. 460-485, vol. 232.

Winslow, R. M., "alphaalpha-Crosslinked Hemoglobin: Was Failure Predicted by Preclinical Testing?" Vox Sanguinis, 2000, pp. 1-20, vol. 79, No. 1.

Winslow, R. M., et al., "Hemoglobin Oxygen Affinity and the Design of Red Cell Substitutes," Advances in Blood Substitutes, Chapter 9, 1997, pp. 167-188.

Winslow, R. M., et al., "Oxygen Equilibrium Curve of Normal Human Blood and Its Evaluation by Adair's Equation," The Journal of Biological Chemistry, Apr. 1977, pp. 2331-2337, vol. 252, No. 7.

Winslow, R. M., et al., "Vascular Resistance and the Efficacy of Red Cell substitutes in a Rat Hemorrhage Model," Journal of Applied Physiology, Sep. 1998, pp. 993-1003, vol. 85, No. 3.

* cited by examiner

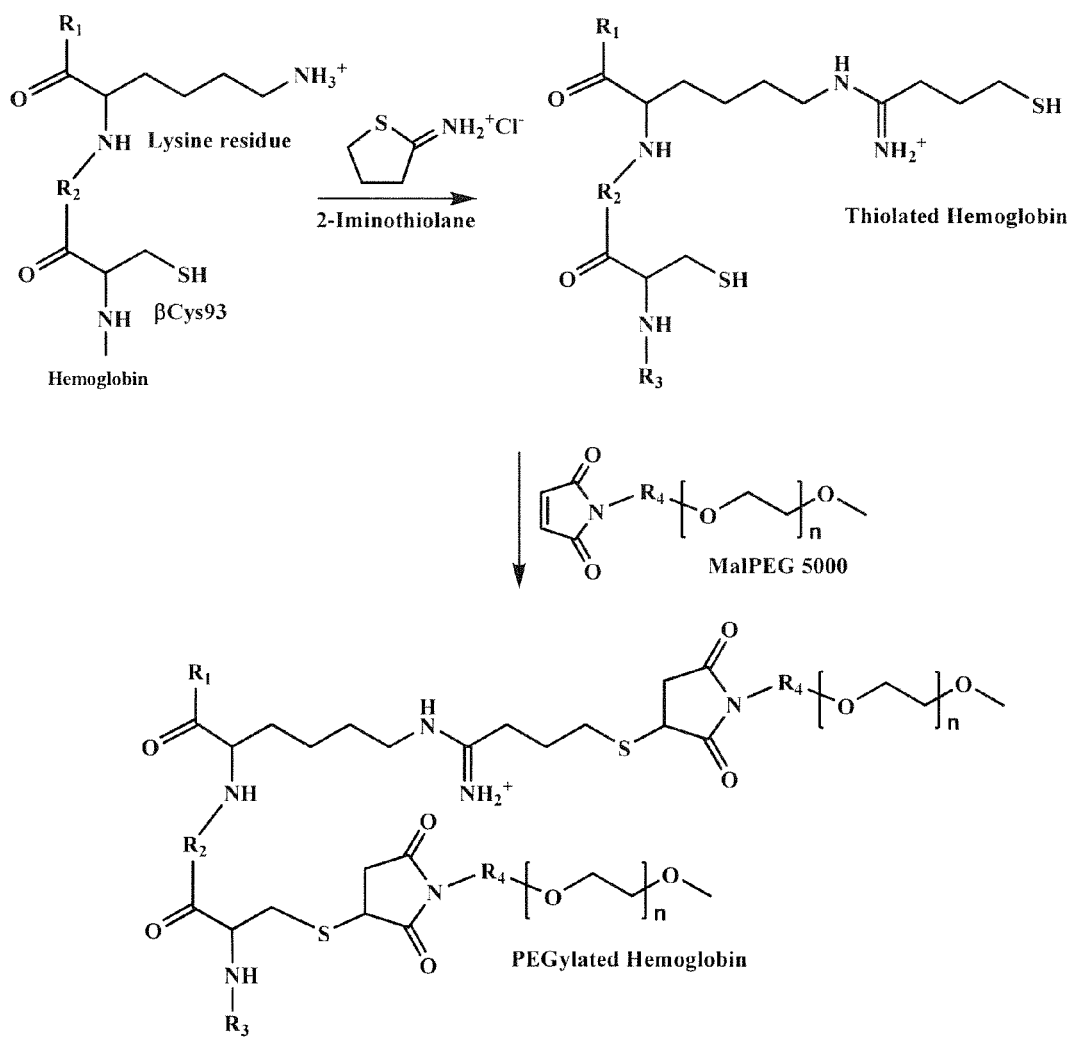

METHODS FOR PREPARING PEG-HEMOGLOBIN CONJUGATES USING REDUCED REACTANT RATIOS

CROSS-REFERENCE TO RELATED APPLICATIONS

This application is a United States national stage entry of International Application serial no. PCT/US2011/25888 filed Feb. 23, 2011, which claims priority to U.S. provisional patent application No. 61/308,238 filed Feb. 25, 2010. The contents of both of these prior applications are incorporated herein by reference in their entirety as if set forth verbatim.

TECHNICAL FIELD

The present invention relates generally to methods for preparing polyethylene glycol ("PEG") conjugated hemoglobin ("Hb") using reduced reactant ratios. More specifically, the present invention relates to methods for preparing PEG conjugated Hb ("PEG-Hb") with enhanced yield and purity.

BACKGROUND OF THE INVENTION

Oxygen carriers that are useful as oxygen therapeutics (sometimes referred to as "oxygen-carrying plasma expanders") can be grouped into the following three categories: i) perfluorocarbon-based emulsions, ii) liposome-encapsulated Hb and iii) modified Hb. As discussed below, none has been entirely successful, though products comprising modified cell-free Hb are thought to be the most promising. Perfluorochemical-based emulsions dissolve oxygen as opposed to binding it as a ligand. In order to be used in biological systems, the perfluorochemical must be emulsified with a lipid, typically egg-yolk phospholipid. Though the perfluorocarbon emulsions are inexpensive to manufacture, they do not carry sufficient oxygen at clinically tolerated doses to be effective. Conversely, while liposome-encapsulated Hb has been shown to be effective, it is too costly for widespread use. (See generally, Winslow, R. M., "Hemoglobin-based Red Cell Substitutes," Johns Hopkins University Press, Baltimore (1992)).

Initial attempts to utilize free Hb from erythrocyte hemolysates as a red cell substitute were unsuccessful. The stromal components were found to be toxic, resulting in coagulopathy and associated renal failure. In 1967, stroma-free Hb ("SFH") solutions had been prepared (Rabiner, S. F. et al., 1967, J. Exp. Med. 126:1127-1142). However, they were found to have a transfusion half-life of only about 100 minutes.

The reason for the short circulation half-life of SFH is due to the ability of the protein to dissociate from its tetrameric form into dimers, which are rapidly filtered from the circulation by the kidneys. Accordingly, a multitude of methods for cross-linking Hb, and other means for increasing the hydrodynamic size of Hb by conjugation with macromolecules, have been devised to limit or prevent the extravasation of Hb. Cross-linking SFH to form poly-Hb is described in U.S. Pat. Nos. 4,001,200 and 4,001,401. Internally cross-linked Hb, which binds amino acid residues between subunits, may be achieved with diaspirin (diesters of bis-3,5-dibromosaliocylate) as described in U.S. Pat. No. 4,529,719) or 2-N-2-formyl-pyridoxal-5'-phosphate and borohydride (Benesch, R. E. et al, 1975, Biochem. Biophys. Res. Commun. 62:1123-1129). Intramolecular cross-linking, which chemically binds subunits of the tetrameric Hb unit to prevent the formation of dimers, is disclosed in U.S. Pat. No. 5,296,465. In addition, Simon, S. R. and Konigsberg, W. H. disclosed the use of bis-(N-maleimidomethyl) ether ("BME") to generate intramolecularly cross-linked Hb (1966, PNAS 56:749-56) that was reported to have a four fold increase in half-life when infused into rats and dogs (Bunn, H. F. et al., 1969, J. Exp. Med. 129:909-24). However, the cross-linking of Hb with BME resulted in the concomitant increase in the oxygen affinity of Hb, which at the time was thought to prevent its use as a potential Hb-based oxygen carrier ("HBOC").

SFH was also linked to other macromolecules such as dextran (Chang, J. E. et al., 1977, Can. J. Biochem. 55:398-403), hydroxyethyl starch (DE 2,161,086), gelatin (DE 2,449,885), albumin (DE 2,449,885) and PEG (DE 3,026,398, U.S. Pat. Nos. 4,670,417, 4,412,989 and 4,301,144).

Some of the physiological effects of these oxygen carrying solutions are not fully understood. Of these, perhaps the most controversial is the propensity to cause vasoconstriction, which may manifest as hypertension in animals and man (Amberson, W., 1947, Science 106:117-117) (Keipert, P. et al., 1993, Transfusion 33:701-708). Human Hb cross-linked between α-chains with bis-dibromosalicyl-fumarate ("ααHb") was developed by the U.S. Army as a model red cell substitute, but was abandoned after it showed severe increases in pulmonary and systemic vascular resistance (Hess, J. et al., 1991, Blood 78:356A). A commercial version of this product was also abandoned after a disappointing Phase III clinical trial (Winslow, R. M., 2000, Vox Sang 79:1-20).

The most common explanation for the vasoconstriction produced by cell-free Hb is that it readily binds the endothelium-derived relaxing factor (EDRF), nitric oxide ("NO"). Two molecular approaches have been advanced in attempting to overcome the NO binding activity of Hb. The first approach was utilizing recombinant DNA, which attempted to reduce the NO binding of Hb by site-specific mutagenesis of the distal heme pocket (Eich, R. F. et al., 1996, Biochem. 35:6976-83). The second approach utilized chemical modification in which the size of the Hb was enhanced through oligomerization, which attempted to reduce or possibly completely inhibit the extravasation of Hb from the vascular space into the interstitial space (Hess, J. R. et al., 1978, J. Appl. Physiol. 74:1769-78; Muldoon, S. M. et al., 1996, J. Lab. Clin. Med. 128:579-83; Macdonal, V. W. et al., 1994, Biotechnology 22:565-75; Furchgott, R., 1984, Ann. Rev. Pharmacol. 24:175-97; and Kilbourne, R. et al., 1994, Biochem. Biophys. Res. Commun. 199:155-62).

In fact, recombinant Hbs with reduced affinity for NO have been produced that are less hypertensive in top-load rat experiments (Doherty, D. H. etg al. 1998, Nature Biotechnology 16:672-676 and Lemon, D. D. et al. 1996, Biotech 24:378). However, studies suggest that NO binding may not be the only explanation for the vasoactivity of Hb. It has been found that certain large Hb molecules, such as those modified with PEG, were virtually free of the hypertensive effect, even though their NO binding rates were identical to those of the severely hypertensive ααHb (Rohlfs, R. J. et al. 1998, J Biol. Chem. 273:12128-12134). Furthermore, it was found that PEG-Hb was extraordinarily effective in preventing the consequences of hemorrhage when given as an exchange transfusion prior to hemorrhage (Winslow, R. M. et al. 1998, J. Appl. Physiol. 85:993-1003).

The conjugation of PEG to Hb reduces its antigenicity and extends its circulation half-life. However, the PEG conjugation reaction has been reported to result in dissociation of Hb tetramers into αβ-dimer subunits causing gross hemoglobinuria in exchange-transfused rats receiving PEG-conjugates of Hb monomeric units below 40,000 Daltons ("Da") (Iwashita and Ajisaka Organ-Directed Toxicity: Chem. Indicies Mech., Proc. Symp., Brown et al. 1981, Eds. Pergamon, Oxford, England pgs 97-101). A polyalkylene oxide ("PAO") conjugated Hb having a molecular weight greater than 84,000 Da was prepared by Enzon, Inc. (U.S. Pat. No. 5,650,388) that carried 10 copies of PEG-5,000 chains linked to Hb at its α and ε-amino groups. This degree of substitution was described as avoiding clinically significant nephrotoxicity associated with hemoglobinuria in mammals. However, the conjugation reaction resulted in a heterogeneous conjugate population and contained other undesirable reactants that had to be removed by column chromatography.

PEG conjugation is typically carried out through the reaction of an activated PEG with a functional group on the surface of biomolecules. The most common functional groups are the amino groups of lysine and histidine residues, and the N-terminus of proteins; thiol groups of cysteine residues; and the hydroxyl groups of serine, threonine and tyrosine residues and the C-terminus of the protein. PEG is usually activated by converting the hydroxyl terminus to a reactive moiety capable of reacting with these functional groups in a mild aqueous environment. One of the most common monofunctional PEGs used for conjugation of therapeutic biopharmaceuticals is methoxy-PEG ("mPEG"), which has only one functional group (i.e. hydroxyl), thus minimizing cross-linking and aggregation problems that are associated with bifunctional PEG. However, mPEG is often contaminated with high molecular weight bifunctional PEG (i.e. "PEG diol"), which can range as high as 10 to 15% (Dust J. M. et al. 1990, Macromolecule 23:3742-3746), due to its production process. This bifunctional PEG diol has roughly twice the size of the desired monofunctional PEG. The contamination problem is further aggravated as the molecular weight of PEG increases. The purity of mPEG is especially critical for the production of PEGylated biotherapeutics, because the FDA requires a high level of reproducibility in the production processes and quality of the final drug product.

Conjugation of Hb to PAOs has been performed in both the oxygenated and deoxygenated states. U.S. Pat. No. 6,844,317 describes conjugating Hb in the oxygenated, or "R" state, to enhance the oxygen affinity of the resultant PEG-Hb conjugate. This is accomplished by equilibrating Hb with the atmosphere prior to conjugation. Others describe a deoxygenation step prior to conjugation to diminish the oxygen affinity and increase structural stability enabling the Hb to withstand the physical stresses of chemical modification, diafiltration and/or sterile filtration and sterilization (U.S. Pat. No. 5,234,903). For intramolecular cross-linking of Hb, it is suggested that deoxygenating Hb prior to modification may be required to expose lysine 99, of the α-chain, to the cross-linking reagent (U.S. Pat. No. 5,234,903).

The kinetics of Hb thiolation with iminothiolane prior to conjugation with PEG was investigated by Acharya et al. (U.S. Pat. No. 7,501,499). It was observed that increasing the concentration of iminothiolane from 10-fold, which introduced an average of five extrinsic thiols per tetramer, to 30-fold nearly doubled the number of extrinsic thiols on Hb. However, the size enhancement seen after PEG conjugation was only marginal, even with double the number of thiols. This suggested that the conjugation reaction in the presence of 20-fold molar excess of maleimidyl PEG-5000 covered the surface of the Hb with less reactive thiols resulting in steric interference that resisted further modification of Hb with more reactive thiols. Consequently, to achieve the desired molecular weight of modified Hb (i.e. 6±1 PEG per Hb molecule), Acharya et al. thiolated Hb with an 8-15 molar excess of iminothiolane, and then reacted the thiolated Hb with a 16-30 fold molar excess of maleimidyl PEG-5000. However, these high molar excess reactant concentrations in large scale production significantly increase the cost for preparing the HBOC. Moreover, such high molar excess of the maleimidyl PEG-5000 results in a more heterogeneous product with the production of a greater number of unwanted reactants.

Accordingly, there is a need for a method of preparing PEG conjugated Hb of a particular size range with decreased cost, increased efficiency, less impurities, and narrower molecular weight range.

SUMMARY OF THE INVENTION

The present invention relates generally to methods for preparing polyethylene glycol conjugated hemoglobin (PEG-Hb) comprising the steps of: mixing hemoglobin (Hb) with 2-iminothiolane (2-IT) in an aqueous diluent, wherein the 2-IT is at a concentration of between 7 and 8 molar excess in the diluent over the Hb concentration, to form thiolated Hb; and then adding polyethylene glycol (PEG)-maleimide (Mal) to the thiolated Hb in the aqueous diluent, wherein the PEG-Mal is at a concentration of between 9 and 15 molar excess in the diluent over the Hb concentration to form a PEG-Hb conjugate, wherein the PEG-Mal has an average molecular weight of between 4,000 and 6,000 Daltons (Da); wherein the resulting PEG-Hb conjugate contains an average of between 7.1 and 8.9 PEG molecules per Hb.

In one embodiment, the 2-IT is at a concentration of 7.5 molar excess in the diluent over the Hb concentration, the PEG-Mal is at a concentration of 12 molar excess in the diluent over the Hb concentration, and/or the PEG-Mal has an average molecular weight of 5,000 Daltons.

The PEG-Hb conjugate prepared according to the exemplary methods of the present invention have a partial pressure of oxygen at which the Hb is 50% saturated (p50) less than native stroma free hemoglobin from an equivalent source when measured under essentially identical conditions. In one embodiment, the p50 of the PEG-Hb conjugate is less than 10 millimeters of mercury (mmHg), such as between 4 and 8 mmHg.

Other aspects of the invention are found throughout the specification.

BRIEF DESCRIPTION OF THE DRAWINGS

FIG. 1: βCys93 residues and thiolated lysines of Hb are PEGylated. $R_1$, $R_2$ and $R_3$ represent the Hb main chain; $R_4$ is an alkyl group, and "n" represents the average number of oxyethylene units of a 5,000 Da PEG.

DETAILED DESCRIPTION OF THE INVENTION

The present invention relates generally to methods for preparing polyethylene glycol ("PEG") conjugated hemoglobin ("Hb") using reduced reactant ratios. More specifically, the present invention relates to methods for preparing PEG conjugated Hb ("PEG-Hb") with enhanced yield and purity.

In the description that follows, a number of terms used in the field of molecular biology, immunology and medicine are extensively utilized. In order to provide a clear and consistent understanding of the specification and claims, including the scope to be given such terms, the following non-limiting definitions are provided.

When the terms "one," "a," or "an" are used in this disclosure, they mean "at least one" or "one or more," unless otherwise indicated.

The term "activated polyalkylene oxide" or "activated PAO" as used herein refer to a PAO molecule that has at least one functional group. A functional group is a reactive moiety that interacts with free amines, sulfhydryls or carboxyl groups on a molecule to be conjugated with PAO. For example, one such functional group that interacts with free sulfhydryls is a maleimide group. Correspondingly, a functional group that interacts with a free amines is a succinimide group.

The term "approximately" as used herein refers to the actual value being within a range of the indicated value. In general, the actual value will be within (i.e. plus or minus) 10% of the indicated value.

The term "hemoglobin" or "Hb" as used herein refer generally to the protein contained within red blood cells that transports oxygen. Each molecule of Hb has 4 subunits, 2 α-chain subunits and 2 β-chain subunits, which are arranged in a tetrameric structure. Each subunit also contains one heme group, which is the iron-containing center that binds oxygen. Thus, each Hb molecule can bind 4 molecules of oxygen.

The term "MalPEG-Hb" as used herein refers to Hb to which maleimidyl-activated PEG has been conjugated. The conjugation is performed by reacting MalPEG with surface thiol groups (and to a lesser extent amino groups) on the Hb to form MalPEG-Hb. Thiol groups are found in cysteine residues present in the amino acid sequence of Hb, and can also be introduced by modifying surface amino groups to contain a thiol group.

The term "methemoglobin" or "metHb" as used herein refer to an oxidized form of Hb that contains iron in the ferric state. MetHb does not function as an oxygen carrier. The term "methemoglobin %" as used herein refers to the percentage of oxidized Hb to total Hb.

The term "methoxy-PEG" or "mPEG" as used herein refer to PEG wherein the hydrogen of the PEG hydroxyl terminus is replaced with a methyl (—$CH_3$) group.

The term "mixture" or "mixing" as used herein refer to a mingling together of two or more substances without the occurrence of a reaction by which they would lose their individual properties. The term "solution" refers to a liquid mixture and the term "aqueous solution" refers to a solution that contains some water and may also contain one or more other liquid substances with water to form a multi-component solution.

The term "modified hemoglobin" or "modified Hb" as used herein refer to, but is not limited to, Hb that is altered by a chemical reaction, such as intra- and inter-molecular cross-linking, recombinant techniques, such that the Hb is no longer in its "native" state. As used herein, the term "hemoglobin" or "Hb" by itself refers both to native unmodified Hb, as well as modified Hb.

The term "oxygen affinity" as used herein refers to the avidity with which an oxygen carrier, such as Hb, binds molecular oxygen. This characteristic is defined by the oxygen equilibrium curve, which relates the degree of saturation of Hb molecules with oxygen (Y axis) with the partial pressure of oxygen (X axis). The position of this curve is denoted by the P50 value, which is the partial pressure of oxygen at which the oxygen carrier is half-saturated with oxygen, and is inversely related to oxygen affinity. Hence, the lower the P50, the higher the oxygen affinity. The oxygen affinity of whole blood (and components of whole blood, such as red blood cells and Hb) can be measured by a variety of methods known in the art. (see, e.g., Winslow, R. M. et al., J. Biol. Chem. 1977, 252:2331-37). Oxygen affinity may also be determined using a commercially available HEMOX™ Analyzer (TCS Scientific Corporation, New Hope, Pa.). (see, e.g., Vandegriff and Shrager in "Methods in Enzymology" (Everse et al., eds.) 232:460 (1994)).

The term "perfluorocarbons" as used herein refers to synthetic, inert, molecules that contain fluorine atoms, and that consist entirely of halogen (Br, F, Cl) and carbon atoms. In the form of emulsions, they are under development as blood substances because they have the ability to dissolve many times more oxygen than equivalent amounts of plasma or water.

The term "polyethylene glycol" or "PEG" as used herein refers to liquid, or solid, polymers of the general chemical formula H(OCH$_2$CH$_2$)$_n$OH (also known as α-Hydro-ω-hydroxypoly-(oxy-1,2-ethanediyl)), where "n" is greater than or equal to 4. Any PEG formulation, substituted or unsubstituted, is encompassed by this term. PEGs are commercially available in a number of formulations (e.g., Carbowax™ (Dow Chemical, Midland, Mich.), Poly-G® (Arch Chemicals, Norwalk, Conn.), and Solbase).

The terms "polyethylene glycol conjugated hemoglobin" or "PEG-Hb conjugate" as used herein refer to hemoglobin to which PEG is covalently attached.

The term "stroma-free hemoglobin" or "SFH" as used herein refers to Hb from which all red blood cell membranes have been removed.

The term "surface-modified hemoglobin" as used herein refers to hemoglobin to which chemical groups, usually polymers, have been attached, such as dextran or polyalkylene oxide. The term "surface modified oxygenated hemoglobin" refers to Hb that is in the "R" state when it is surface modified.

Organic Polymers

In previous studies, it was observed that the molecular size of surface modified hemoglobin has to be large enough to avoid being cleared by the kidneys and to achieve the desired circulation half-life. Blumenstein, J. et al., determined that this could be achieved at, or above, a molecular weight of 84,000 Daltons ("Da") ("Blood Substitutes and Plasma Expanders," Alan R. Liss, editors, New York, N.Y., pages 205-212 (1978)). In that study, the authors conjugated dextran of varying molecular weight to Hb. They reported that a conjugate of Hb (with a molecular weight of 64,000 Da) and dextran (having a molecular weight of 20,000 Da) "was cleared slowly from the circulation and negligibly through the kidneys." Further, it was observed that increasing the molecular weight above 84,000 Da did not significantly alter these clearance curves.

The present invention provides methods for the conjugation of PAO to Hb wherein a molecular weight of at least 84,000 Da can be obtained. Suitable polyalkylene oxide polymers include, polyethylene oxide ($-(CH_2CH_2O)_n-$), polypropylene oxide ($-(CH(CH_3)CH_2O)_n-$) and a polyethylene/polypropylene oxide copolymer ($-(CH_2CH_2O)_n-(CH(CH_3)CH_2O)_n-$). Other straight, branched chain and optionally substituted synthetic polymers that would be suitable in the practice of the present invention are well known in the medical field.

The most common PAO presently used to modify the surface of Hb is PEG because of its pharmaceutical acceptability and commercial availability. In addition, PEG is available in a variety of molecular weights based on the number of repeating subunits of ethylene oxide (i.e. $-OCH_2CH_2-$) within the molecule. PEG formulations are usually followed by a number that corresponds to their average molecular weight. For example, PEG-200 has an average molecular weight of 200 Da and may have a molecular weight range of 190-210 Da.

Hemoglobin Modification

The Hb utilized in the present methods is not limited by its source and can be derived from humans or animals, or from recombinant techniques. It may be either native (unmodified) or modified, or recombinantly engineered. Human α- and β-globin genes have both been cloned and sequenced (Liebhaber, S. A. et al., PNAS 1980, 77:7054-7058; Marotta, C. A. et al., J. Biol. Chem. 1977, 353: 5040-5053 (β-globin cDNA)). In addition, many recombinantly modified Hbs have now been produced using site-directed mutagenesis, although these "mutant" Hb varieties were reported to have undesirably high oxygen affinities (e.g., Nagai, K. et al., PNAS 1985, 82:7252-7255). Preferably, the Hb is stroma free and endotoxin free.

One method to increase the number of available conjugation sites on Hb is to introduce sulfhydryl groups ("—SH"), which tend to be more reactive with PEG-Mal than free amines. A variety of methods are known in the art for thiolation of proteins. These include, for example, thiolating free amine containing residues of the protein by reaction with succinimidyl 3-(2-pyridyldithio)propionate followed by reduction of the 3-(2-pyridyldithio)propionyl conjugate with dithiothreitol ("DTT"), or tris(2-carboxyethyl)phosphine ("TCEP"). Amines can also be indirectly thiolated by reaction with succinimidyl acetylthioacetate, followed by removal of the acetyl group with 50 mM hydroxylamine, or hydrazine, at near-neutral pH. In addition, 2-iminothiolane (2-IT) can be used to convert free amine groups into thiol groups.

Native human Hb has a fixed number of amino acid residue side chains that may be accessed for thiolation followed by conjugation to maleimide-activated PAO molecules. These are presented in the chart below:

|  | Alpha Globin |
|---|---|
| Lys | 7, 16 and 40 |
|  | Beta Globin |
| Lys | 8, 17, 59, 66, 95 |
| Cys | 93, 132 |

It has been suggested that it would be beneficial to maintain the original positive charge of the amino (α- or ε-) groups of the Hb after conjugation. To achieve this, a protocol was developed to attach PEG to Hb using the ε-amino groups of its surface lysine residues, where the Hb still retains the original positive charge of the amino groups (U.S. Pat. No. 5,585,484). This involves amidination of the ε-amino groups of Hb by 2-iminothiolane to introduce sulfhydryl groups onto the protein, which are subsequently targeted as the attachment sites for PEG during the conjugation reaction using maleimide-PEG.

This approach has at least two additional specific advantages over the previously used succinimidyl chemistry: (I) the very high reactivity and selectivity of maleimide groups with sulfhydryl groups facilitates the near quantitative modification of the thiols, with a limited excess of reagents; and (2) the thiol group of 2-iminothiolane is latent and is generated only in situ as a consequence of the reaction of the reagent with the protein amino groups. Accordingly, Hb can be incubated simultaneously with the thiolating and PEGylating reagents for surface decoration with PEG.

In one embodiment, the thiolation reaction is carried out at a pH of between 7 to 9, which is below the pH at which the 2-IT hydrolyzes significantly before the reaction is completed and also below the pKa of lysine to optimize the extent of the reaction.

Conjugation

As discussed elsewhere herein, it was previously postulated that increasing the molar ratios of the reactants in the conjugation reaction would result in an increased number of PEG molecules that would become conjugated to Hb. This included both the thiolation process of Hb (i.e. increasing the molar ratio of the thiolating agent to Hb) and the surface modification process (i.e. increasing the molar ratio of activated PEG to thiolated Hb). These studies demonstrated that a greater than 10-fold molar excess of iminothiolane substantially increased the number of thiolated sites on Hb from 4 new reactive —SH groups per tetramer, in the first two hours of the reaction, to about 7 new reactive —SH groups per tetramer after eleven hours. Increasing the molar ratio from 10-fold to 30-fold nearly doubled the total number of thiols on the Hb. Correspondingly, increasing the molar ratio of thiol activated PEG to thiolated Hb (i.e. 20-fold) also increased the number of maleimide activated PEG molecules that could be conjugated to thiolated Hb (see U.S. Pat. No. 7,501,499). These excess molar ratios resulted in Hb having 6±1 PEG molecules covalently bound on its surface. However, increasing reactant ratios as described slows the reaction kinetics, increases the level of undesirable byproducts and increases the molecular weight distribution of the PEG-Hb conjugate.

The present invention is based on the unexpected finding that, with a particular molecular weight PEG and at precisely controlled reactant ratios, a superior PEG-Hb conjugate can be produced. The method of the present invention utilizes reduced molar ratios of reactants in both the Hb thiolation reaction as well as the PEG conjugation reaction. Unexpectedly and contrary to conventional wisdom that a higher concentration of reactants will increase both yield and conjugation efficiency, it was found that a greater number of PEG molecules can be conjugated to modified Hb using lower molar ratios of reactants. And as another benefit, it was found that the resulting conjugation product had a tighter molecular weight distribution than the same product using higher ratios. More specifically, in the thiolation reaction, less than an 8-fold molar excess of 2-IT, particularly between 7- and 8-fold molar excess and more particularly a 7.5-fold molar excess; and in the conjugation reaction, less than a 15-fold molar excess of PEG-Mal, particularly between 9- and 15-fold molar excess and more particularly a 12-fold molar excess; resulted in an average number of PEG molecules per Hb of between 7.1 and 8.9, and particularly about 8. As discussed, using lower molar ratios of reactants has several advantages. It reduces the impurities in the final product, which facilitates the purification process efficiency and increases the reaction efficiency through enhanced molecular dispersion. The increased efficiency also reduces the reaction time for completing hydrolysis and deactivation of the maleimide ring. In addition, by decreasing the amounts of the reactants, the byproducts from their respective reactions are also reduced. Specifically, the hydrolysis byproducts from 2-IT, including 4-butrythiolactone and 4-thiobutyric acid, as well as the ring-opened, nonreactive PEG byproduct are significantly decreased.

As described above, the molar ratio of PEG-Mal to Hb in the conjugation reaction is less than 15-fold. This molar ratio is based on the concentration of reactive PEG-Mal, and is not based on the absolute ratio of PEG-Mal to Hb. The percentage of reactive maleimide with a closed ring structure in the PEG-Mal is referred to as its "terminal activity". Accordingly, if all the malemide is reactive, the PEG-Mal has a terminal activity of 100%. The molar ratio of PEG-Mal to Hb as described herein is based on the molar ratio of terminally active PEG-Mal to Hb. Accordingly, if the terminal activity of the PEG-Mal reagent is 90%, 10% more will need to be added to Hb to achieve the same molar ratio.

Reduction in the residual unreacted PEG has the added benefit of increasing the efficiency in production and the quality of the final product. Following the PEG conjugation reaction, the residual reactants are removed by diafiltration with 10 volumes of final production diluent, such as Ringer's lactate or acetate solution. The amount of time required for this step is determined by the volumetric flux of the diafiltration process. For a given filter size, the diafiltration process is finished faster when the reaction ratios of the present invention are utilized. The washout of the reactants follows an exponential decay and as a result, decreasing the initial concentration of impurities (residual reactants and impurities in the reactants) will decrease their final concentration in the product. Correspondingly, minimizing the total amount of reagents can reduce the total quantity of impurities in the product.

PEG-Hb Conjugate

The PEG-Hb conjugate of the present invention usually has an oxygen affinity greater than whole blood, and more specifically, twice or even thrice that of whole blood. Stated differently, the PEG-Hb usually has an oxygen affinity greater than that of stroma free hemoglobin (SFH), when measured under the same conditions. This means that the PEG-Hb conjugate will generally have a P50 less than 10 millimeters of mercury (mmHg), but greater than 3 mmHg. SFH has a p50 of approximately 15 mmHg at 37° C., pH 7.4, whereas the p50 for whole blood is approximately 28 mmHg under the same conditions. It was suggested that increasing oxygen affinity of a hemoglobin-based oxygen carrier (HBOC), and thereby lowering the p50, could enhance delivery of oxygen to tissues, but that an oxygen affinity lower than that of SFH would not be acceptable. See Winslow, R. M. et al., in "Advances in Blood Substitutes" (1997), Birkäuser, eds. Boston, Mass., at page 167, and U.S. Pat. No. 6,054,427. This suggestion contradicts the widely held belief that HBOCs should have lower oxygen affinities, and specifically p50s that approximate that of whole blood. Hence, many researchers have used pyridoxyl phosphate to raise the p50 of SFH from 10 mmHg to approximately 20-22 mmHg, since pyridoxylated Hb more readily releases oxygen when compared to SFH.

There are many different scientific approaches to manufacturing HBOCs with high oxygen affinity (i.e. those with p50s less than SFH). For example, studies have identified the amino acid residues that play an important role in oxygen affinity, such as $\beta 93$ cysteine. Because of these findings, site-directed mutagenesis can now be easily carried out to manipulate oxygen affinity to the desired level (see, e.g., U.S. Pat. No. 5,661,124). The $\beta 93$ cysteine residue is located immediately adjacent to the proximal $\beta 92$ histidine residue, which is the only residue in the $\beta$-subunit directly, coordinated to the heme iron. Attachment of the rigid, bulky maleimide group to the $\beta 93$ cysteine displaces a salt bridge that normally stabilizes the low-affinity T-state Hb conformation (Perutz M. F. et al., Biochemistry 1974, 13:2163-2173). This shifts the quaternary conformation towards the R state, resulting in higher $O_2$ affinity (Imai, K. et al., Biochemistry 1973, 12:798-807). Many other approaches are discussed in U.S. Pat. No. 6,054,427.

Formulation for In Vivo Administration

The PEG-Hb conjugate of the present invention is formulated in an aqueous diluents that is suitable for in vivo administration. Although the concentration of the oxygen carrier in the diluent may vary according to the application, it does not usually exceed a concentration of 10 g/dl of Hb, because of the enhanced oxygen delivery and therapeutic effects of the PEG-Hb conjugate. More specifically, the concentration is usually between 0.1 and 8 g/dl Hb.

Suitable aqueous diluents (i.e., those that are pharmaceutically acceptable for intravenous injection) include, inter alia, aqueous solutions of proteins, glycoproteins, polysaccharides, and other colloids. It is not intended that these embodiments be limited to any particular diluent. Consequently, diluents may encompass aqueous cell-free solutions of albumin, other colloids, or other non-oxygen carrying components.

This solution property of a PEG-Hb conjugate is due to the strong interaction between PEG chains and solvent water molecules. This is believed to be an important attribute for an HBOC for two reasons: 1) higher viscosity decreases the diffusion constant of both the PEG-Hb molecule, and 2) higher viscosity increases the shear stress of the solution flowing against the endothelial wall, eliciting the release of vasodilators to counteract vasoconstriction. Accordingly, the formulation of PEG-Hb in the aqueous diluent usually has a viscosity of at least 2 centipoise (cP). More specifically, between 2 and 4 cP, and particularly around 2.5 cP. In other embodiments, the viscosity of the aqueous solution may be 6 cP or greater, but is usually not more than 8 cP.

The PEG-Hb conjugate is suitable for use as a hemoglobin-based oxygen carrier as is any other such product. For example, it is useful as a blood substitute, for organ preservation, to promote hemodynamic stability during surgery, etc.

EXAMPLES

Example 1

Thiolation of Hb

1. Production of SFH

Packed red blood cells ("RBCs") are procured from a commercial source, such as from a local Blood Bank, the New York Blood Center, or the American Red Cross. The material is obtained not more than 45 days from the time of collection. All units are screened for viral infection and subjected to nucleic acid testing prior to use. Non-leukodepleted pooled units are leukodepleted by membrane filtration to remove white blood cells. Packed RBCs are pooled into a sterile vessel and stored at 2-15° C. until further processing. The volume is noted, and Hb concentration is determined using a commercially available co-oximeter, or other art-recognized method.

RBCs are washed with six volumes of 0.9% sodium chloride using a 0.45-μm tangential flow filtration, followed by cell lysis by decreasing the concentration of salt. Hb extraction is performed using the same membrane. The cell wash is analyzed to verify removal of plasma components by a spectrophotometric assay for albumin. The lysate is processed through a 0.16-μm membrane in the cold to purify Hb. The purified Hb is collected in a sterile depyrogenated and then ultrafiltered to remove virus. Additional viral-reduction steps, including solvent/detergent treatment, nanofiltration, and anion Q membrane purification may be performed. All steps in this process are carried out at 2-15° C.

Hb from lysate is exchanged into Ringers lactate ("RL"), or phosphate-buffered saline ("PBS", pH 7.4), using a 30-kD membrane. The Hb is concentrated to 1.1-1.5 mM (in tetramer). Ten to 12 volumes of RL or PBS are used for solvent exchange. This process is carried out at 2-15° C. The pH of the solution prepared in RL or PBS is adjusted to 8.0 prior to thiolation. The Hb is sterile-filtered through a 0.45 or 0.2-μm disposable filter capsule and stored at 4±2° C. before the chemical modification reaction is performed.

2. Thiolation of the SFH

Using the SFH prepared as described above, thiolation is carried out using less than 8-fold molar excess of 2-IT over Hb. The ratio and reaction time are optimized to maximize the number of thiol groups for PEG conjugation and to minimize product heterogeneity. Approximately 1 mM Hb (tetramer) in RL (pH 7.0-8.5), PBS or any similar buffer, is combined with less than 8 mM 2-IT in the same buffer. This mixture is continuously stirred for less than 6 hours at 10±5° C.

The dithiopyridine colorimetric assay (Ampulski, R. S. et al., Biochem. Biophys. Acta 1969, 32:163-169) is used to measure the number of available thiol groups on the surface of the Hb tetramer before and after thiolation, and then again after Hb-PEG conjugation. Human Hb contains two intrinsic reactive thiol groups at the β93 cysteine residues, which is confirmed by the dithiopyridine reaction. After thiolation of SFH at a ratio of 1:<8 (SFH: 2-IT), the number of reactive thiol groups increases from two to greater than seven thiols.

Example 2

Conjugation of Hb to PEG-Mal

PEG-Mal is conjugated to the thiolated Hb from Example 1 using less than a 15-fold molar excess of PEG-Mal based on 100% terminal activity over the starting tetrameric Hb concentration. The Hb is first allowed to equilibrate with the atmosphere to oxygenate the Hb. Approximately, 1 mM thiolated Hb in RL (pH 7.0-8.5), PBS or any similar buffer is combined with less than 15 mM PEG-Mal in the same buffer. This mixture is continuously stirred for less than 6 hours at 10±5° C.

PEG-Hb conjugate is processed through a 70-kD membrane (i.e. <0-volume filtration) to remove unreacted reagents. This process is monitored by size-exclusion liquid chromatography ("LC") at 540 nm and 280 nm. The concentration is adjusted to 4 g/dl Hb and the pH is adjusted to 6.0±7.8.

The final PEG-Hb conjugate product is sterile filtered using a 0.2-μm sterile disposable capsule and collected into a sterile depyrogenated vessel at 4±2° C. The PEG-Hb conjugate is diluted to 4 g/dl RL and the pH adjusted to 7.4±0.2 pH and then sterile-filtered (0.2 μm) and aliquoted into endotoxin free sterile containers.

Example 3

Characterization of the PEG-Hb Conjugate

1. Methodology for Physiochemical Analysis

Homogeneity and molecular size of the PEG-Hb conjugate are characterized by LC to evaluate the removal of unreacted PEG-Mal. The amount of Hb in the eluate is determined by monitoring absorbance at 540 nm. This resolves PEG-Hb conjugate from unreacted Hb by peak position based on their molecular weight difference. The amount of unreacted PEG-Mal in the eluate is determined by monitoring absorbance at 280 nm. This resolves PEG-Hb conjugate from free PEG-Mal, which absorbs in the ultraviolet ("UV") region of the spectrum due to the maleimide ring structure in PEG-Mal.

Optical spectra are collected using a rapid scanning diode array spectrophotometer in the Soret and visible regions for analysis of Hb concentration and percent metHb by multicomponent analysis.

PEG-Hb conjugate concentration and percentage metHb are determined using a co-oximeter (Instrumentation Laboratory, Bedford, Mass.) Viscosity is determined using a Rheometer (Brookfield Engineering Laboratories, Inc. Middleboro, Mass.)). Colloid osmotic pressure is determined using a colloid osmometer, Osmomat 050 (Gonotec GmbH, Germany). Oxygen binding parameters are determined from oxygen equilibrium curves using a Hemox Analyzer (TCS Scientific Corporation, New Hope, Pa.).

2. Specifications for a PEG-Hb Conjugate

The specification for an exemplary blood substitute composition of the present invention is presented in Table 1 below:

TABLE 1

| Test | Specification |
| --- | --- |
| Hemoglobin Concentration (g/dL) | 4.0 to 4.6 |
| Methemoglobin (%) | <10 |
| pH | 6.4 to 7.9 |
| Osmolality (mOsm/L) | 240 to 300 |
| Endotoxin (EU/mL) | <0.5 |
| Purity by GPC | >95% |
| Viscosity (cPs) | 2 to 4 |
| Colloidal Osmotic Pressure (mmHg) | 60-70 |
| p50 (mmHg) | 5 ± 2 |
| Hill Number (at p50) | 1.2 ± 0.5 |
| Degree of PEG conjugation | Average between 7.1 and 8.9 PEGs/Hb tetramer |
| Bohr Effect (delta Log) | −0.24 |
| Molecular Weight (kDa) | >100 |
| Sterility | Pass |

The examples set forth above are provided to give those of ordinary skill in the art with a complete disclosure and description of how to make and use the preferred embodiments of the compositions, and are not intended to limit the scope of what the inventors regard as their invention. Modifications of the above-described modes (for carrying out the invention that are obvious to persons of skill in the art) are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method for preparing polyethylene glycol conjugated hemoglobin (PEG-Hb) comprising the steps of:
   a) mixing hemoglobin (Hb) with 2-iminothiolane (2-IT) in an aqueous diluent, wherein the 2-IT is at a concentration of between 7- and 8-fold molar excess in the diluent over the Hb concentration, to form thiolated Hb; and
   b) adding polyethylene glycol (PEG)-maleimide (Mal) to the thiolated Hb in the aqueous diluent, wherein the PEG-Mal is at a concentration of between 9- and 15-fold molar excess in the diluent over the Hb concentration to form a PEG-Hb conjugate, wherein the PEG-Mal has an average molecular weight of between 4,000 and 6,000 daltons (Da);
   wherein the PEG-Hb conjugate contains an average of between 7.1 and 8.9 PEG molecules per Hb.

2. The method according to claim 1, wherein the 2-IT is at a concentration of 7.5-fold molar excess in the diluent over the Hb concentration.

3. The method according to claim 1, wherein the PEG-Mal is at a concentration of 12-fold molar excess in the diluent over the Hb concentration.

4. The method according to claim 1, wherein the PEG-Mal has an average molecular weight of 5,000 Da.

5. The method according to claim 1, wherein the PEG-Hb conjugate has a partial pressure of oxygen at which the Hb is 50% saturated (p50) less than native stroma free hemoglobin from an equivalent source when measured under essentially identical conditions.

6. The method according to claim 5, wherein the p50 of the PEG-Hb conjugate is less than 10 millimeters of mercury (mmHg).

7. The method according to claim 5, wherein the p50 of the PEG-Hb conjugate is between 4 and 8 mmHg.

8. The method according to claim 5, wherein step a) is carried out at a pH of between 7 and 9.

9. The method according to claim 1, wherein the maleimide is linked to the PEG via an alkylene linker.

10. The method according to claim 1, wherein the PEG-Hb has the structure:

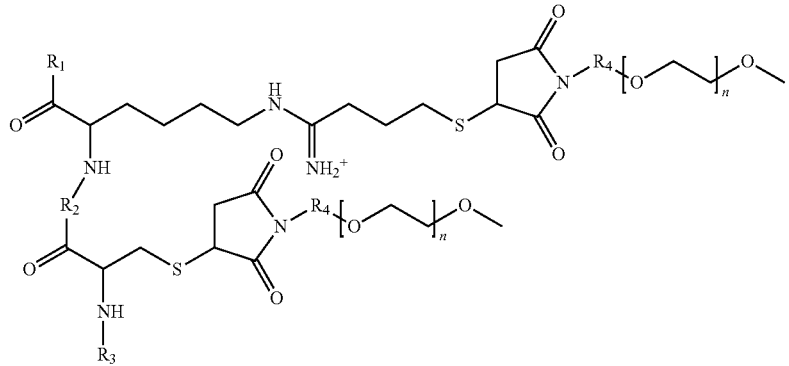

wherein $R_1$, $R_2$, and $R_3$ represent the Hb main chain, $R_4$ is an alkylene group, and n represents the average number of oxyethylene units of PEG.

11. The method according to claim 1, wherein the 2-IT is at a concentration of 7.5-fold molar excess in the diluent over the Hb concentration and the PEG-Mal is at a concentration of 12-fold molar excess in the diluent over the Hb concentration.

12. The method according to claim 11, wherein step a) is carried out at a pH of between 7 and 9.

13. The method according to claim 11, wherein the PEG-Mal has an average molecular weight of 5,000, and the p50 of the PEG-Hb conjugate is between 4 and 8 mmHg Da.

14. The method according to claim 11, wherein the maleimide is linked to the PEG via an alkylene linker.

15. The method according to claim 13, wherein the maleimide is linked to the PEG via an alkylene linker.

16. The method according to claim 11, wherein the PEG-Hb has the structure:

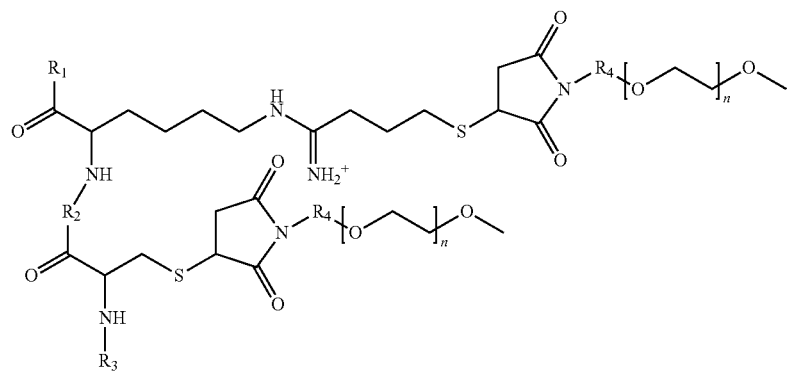

wherein $R_1$, $R_2$, and $R_3$ represent the Hb main chain, $R_4$ is an alkylene group, and n represents the average number of oxyethylene units of PEG.

17. The method according to claim 13, wherein the PEG-Hb has the structure:

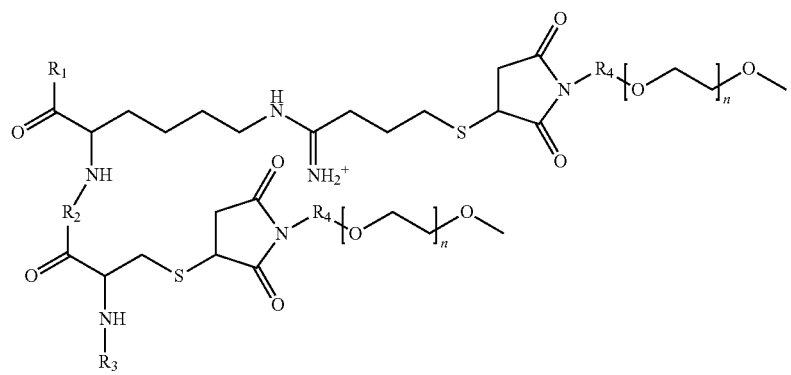

wherein $R_1$, $R_2$, and $R_3$ represent the Hb main chain, $R_4$ is an alkylene group, and n represents the average number of oxyethylene units of PEG.

18. A method for preparing polyethylene glycol conjugated hemoglobin (PEG-Hb) comprising the steps of:
a) mixing hemoglobin (Hb) with 2-iminothiolane (2-IT) in an aqueous diluent, wherein the 2-IT is at a concentration of between 7- and 8-fold molar excess in the diluent over the Hb concentration, to form thiolated Hb; and
b) adding polyethylene glycol (PEG)-maleimide (Mal) to the thiolated Hb in the aqueous diluent, wherein the PEG-Mal is at a concentration of between 9- and 15-fold molar excess in the diluent over the Hb concentration to form a PEG-Hb conjugate, wherein the PEG-Mal has an average molecular weight of 5,000 daltons (Da); the PEG-Hb conjugate contains an average of between 7.1 and 8.9 PEG molecules per Hb; the PEG-Hb has the structure:

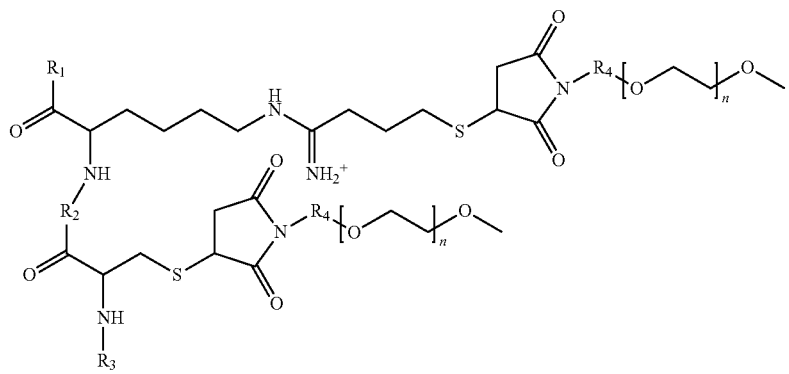

wherein $R_1$, $R_2$, and $R_3$ represent the Hb main chain, $R_4$ is an alkylene group, and n represents the average number of oxyethylene units of PEG.

* * * * *